United States Patent [19]
Benson et al.

[11] Patent Number: 5,830,709
[45] Date of Patent: *Nov. 3, 1998

[54] DETECTION METHOD FOR HOMOLOGOUS PORTIONS OF A CLASS OF SUBSTANCES

[76] Inventors: Roger E. Benson, 23 Delafield St., Albany, N.Y. 12205; James L. Catalfamo, 10 South St., South Bethlehem, N.Y. 12161; W. Jean Dodds, 938 Stanford St., Santa Monica, Calif. 90403

[ * ] Notice: The term of this patent shall not extend beyond the expiration date of Pat. No. 5,196,311.

[21] Appl. No.: 35,452

[22] Filed: Mar. 23, 1993

Related U.S. Application Data

[63] Continuation-in-part of Ser. No. 604,885, Oct. 26, 1990, Pat. No. 5,202,264, which is a continuation-in-part of Ser. No. 428,161, Oct. 27, 1989, Pat. No. 5,196,311.

[51] Int. Cl.$^6$ .......................... G01N 33/537; G01N 33/53
[52] U.S. Cl. ........................... 435/7.92; 435/7.1; 435/7.4; 435/7.5; 435/7.9; 435/7.94; 436/501
[58] Field of Search ................................ 435/7.94, 7.92, 435/7.9, 7.5, 7.4, 7.1; 436/501

[56] References Cited

U.S. PATENT DOCUMENTS

| | | | |
|---|---|---|---|
| 4,376,110 | 3/1983 | David et al. | 436/513 |
| 4,486,530 | 12/1984 | David et al. | 436/519 |
| 4,578,218 | 3/1986 | Saundry et al. | 530/383 |
| 4,666,865 | 5/1987 | Chang et al. | 436/518 |
| 4,687,747 | 8/1987 | Lin | 436/518 |
| 4,748,110 | 5/1988 | Paul | 435/5 |
| 4,789,804 | 12/1988 | Karube et al. | 310/311 |
| 5,208,024 | 5/1993 | Van Den Bosch | 424/92 |
| 5,514,599 | 5/1996 | Mullner | 436/518 |

OTHER PUBLICATIONS

Dore et al., "Immunochemical studies of tobacco mosaic virus—VII. Use of comparative surface accessibility of residues in antigenically related viruses for delineating epitopes recognized by monoclonal antibodies," Molecular Immunology 24: 1351–1358 (1987).

Dekker et al., "Limitation of different ELISA procedures for localizing epitopes in viral coat protein subunits," Arch Virol 105:269–286 (1989).

Hornsey et al., "Enhancement of Factor VIII von Willebrand Factor Ristocetiu Cofactor . . . ," Thrombosis & Haemostasis 54: 510–514 (1985).

Furlan et al., "Exposure of Platelet Binding Sites in von Willebrand . . . ," Biochim. Biophys. Acta 924:27–37 (1987).

Barkas et al., "Induction of an $F_c$ Conformational Change . . . ," Immunology 36:557–561 (1979).

Katzmann et al., "Monoclonal Centibodies to von Willebrand . . . ," Blood 58:530–536 (1981).

Suter et al., "The Immunochemistry of Sandwich ELISA . . . ," Immunol Lett. 13:313–316 (1986).

Benjamin et al., "A Unique Epitope on Human Servin Albumin Recognized by Monoclonal . . . ," Hybridoma 6:183–190 (1987).

Silveira et al., "Application of An Enzyme–Linked Immunosorbent Assay . . . ," Thrombosis Research 43:91–102 (1986).

Benson et al., "A Multispecies Enzyme–Linked Immunosorbent Assay . . . ," J Lab Clin Med 119:420–28 (1992).

VanRegenmortel, "Structure of Virol B–cell Epitopes," Res. Microbiol. 141: 747–756.

Mullner et al., "A radioimmunoassay for the determination of insulins from several animal species, insulin derivatives and insulin precursors in both their native and denatured state," J Immunological Methods 140 (1991).

Groyer–Picard et al., "Monoclonal antibodies for immunocytochemistry of progesterone receptors (PR) in various laboratory rodents, livestock, humans, and chickens: identification of two epitopes conserved in PR of all these species," Endocrinology, (1990 Mar.) 126(3) 1485–91.

Davis et al., The development and analysis of species specific and cross reactive monoclonal antibodies to leukocyte differentiation antigens and antigens of the major histocompatibility complex for use in the study of the immune system in cattle and other species, Veterinary Immunology and Immunopathology, (1987 Jul.) 15 (4) 337–76.

Patterson–Allen et al., "A specific radioimmunoassay for osteocalcin with advantageous species crossreactivity," Analytical Biochemistry, (1982 Feb.) 120 (1) 1–7.

Ardaillou, N., et al., Thrombosis Research 12: 817–830 (1978).

Bartlett, A., et al., Br Med J 1: 994–996 (1976).

Benson, R.E., et al., Thrombosis Research 7: 383–389 (1975).

Benson, R.E., et al., Amer. J. Vet. Research 44: 399–403 (1983).

Benson,R.E., et al., Vet.Immunology & Immunopath. 7:337–346 (1984).

Benson, R.E. & Dodds, W.J., Vet.Immun. &Immunopath 11:21–30 (1986).

Bowie, E.J.W., et al., Blood 62: 146–151 (1983).

(List continued on next page.)

*Primary Examiner*—Michael P. Woodward
*Attorney, Agent, or Firm*—Merchant, Gould, Smith, Edell, Welter & Schmidt

[57] ABSTRACT

The invention provides a method of detecting a class of substances, by providing an assay configuration which allows for reaction with a homologous portion common to all members of the class. The configuration utilizes a capture reactant to immobilize class members, revealing previously unrecognizable reaction sites on the class. The capture reactant interacts with a homologous portion on the class members. The immobilized class is then detected, such as by the use of a sandwich antibody directed to another homologous portion of the class now exposed for reaction, or directed to specific portions of specific members of the class that have been exposed for reaction. These reaction sites were unrecognizable prior to immobilization of the class members with the capture reactant.

14 Claims, 2 Drawing Sheets

OTHER PUBLICATIONS

Bradley, L.A., et al., Clin. Chem. 30: 87–92 (1984).
Brien, W.F., & Stewart, M.W., Clin. Biochemistry 19;179–182 (1986).
Brown, J.E., & Bosak, J.O., Thrombosis Research 43:303–311 (1986).
Casonoto, A., & Girolami, A., Folia Haematol. 113: 670–684 (1986).
Cejka, J., Clin. Chem. 28: 1356–1358 (1982).
Fishman, D.J., et al., Blood 59: 1163–1168 (1982).
Furlong, R.A., et al., Clin. lab. Haemat. 10: 295–305 (1988).
Handin, R.I., & Wagner, D.D., Progress in Hemostasis and Thrombosis 9: 233–259 (1989).
Ingerslev, J., Scand J Clin Lab Invest 47: 143–149 (1987).
Ingerslev, J., et al., Clinica Chimica Acta 174: 65–82 (1988).
Inoue, K., et al., Chem. Pharm. Bull. 34: 2550–2554 (1986).
Katzmann, J.A., et al., Blood 58: 530–536 (1981).
Mascelli, M.A., et al., Biochemistry 25: 6325–6335 (1986).
Mascelli, M.A., & Kirby, E.P., Biochemistry 27: 1274–1284 (1988).
Meyers, K.M., et al., Thrombosis Research 57: 109–116 (1990).
Ness, P.M., & Perkins, H.A., Thrombos.Haemostas. 42:848–853 (1979).
Ogata, K., et al., Blood 62: 27–35 (1983).
Peake, I.R., & Bloom, A.L., Thrombosis Research 10: 27–32 (1977).
Rodeghiero, F., et al., Blood 69: 454–459 (1987).
Short, P.E., et al., Medical Lab. Sciences 39: 351–355 (1982).
Silveira, A.M.V., et al., Thrombosis Research 43: 91–102 (1986).
Taylor, L.D., Thrombosis and Haemostasis 59: 251–254 (1988).
Wang, H.X., et al., J Clin Pathol 38: 317–319 (1985).
Yamamoto, T., et al., Thrombosis Research 45: 59–74 (1987).
Yorde, L.D., et al., Clin. Chem. 25: 1924–1927 (1979).
Zimmerman, T.S., et al., J. Lab. Clin. Med. 86: 152–159 (1975).
Zimmerman, T.S., et al., J.Clin. Investigation 50: 244–254 (1971).
Bennett, B. and Ratnoff, W.D., Proc Soc Exp Biol Med 143: 701–706 (1973).
Benson, R.E. & Dodds, W.J., Br J Haematol 31: 437–446 (1975).
Bouma, B.N., et al., Scand J Haematol 17: 263–275 (1976).
Clowes, A.W., et al., Lab Invest 39: 141–149 (1978).
Coppola, R., et al., Thrombosis Research 17: 473–480 (1980).
Cotter, S.M., et al., J Am Vet Assoc 172: 166–168 (1978).
Griggs, T.R., et al., Proc. Natl Acad Sci USA 74: 759–763 (1977).
Johnson, G.S., et al., Thrombosis Research 42: 419–423 (1986).
Meyer, D., et al., Br J Haematol 57: 597–608 (1984).
Nachman, R., et al., J Clin Invest 60: 914–920 (1977).
Olson, J.D., et al., J Lab Clin Med 89: 1278–1293 (1977).
Schmer, G., et al. J Biol Chem 247: 2512–2521 (1972).
Turitto, V.T., et al., Blood 65: 823–831 (1985).
Verweij, C., et al., EMBO J. 5: 1839–1847 (1986).
Pietu, G., et al., Biochem Biophys Res Comm 163: 618–626 (1989).
Bahou, W., et al., J Clin Invest 84: 56–61 (1989).
Brinkhous, K., et al., Embase Abstract No. 86008826 of Semin Thromb Hemost 11: 337–341 (1985).
Chand, S., et al., Embase Abstract No. 86198216 of Throm Haemostasis 55: 318–324 (1986).
Thorsen, L., et al., Embase Abstract No. 84035971 of Throm Haemostasis 57: 212–216 (1987).
Silverman, C., et al., J Lab Clin Med 110: 113–118 (1987).

DETECTION METHOD FOR HOMOLOGOUS PORTIONS OF A CLASS OF SUBSTANCES

This application is a continuation-in-part of U.S. Ser. No. 07/604,885, filed Oct. 26, 1990, now U.S. Pat. No. 5,202,264, which was a continuation-in-part of Ser. No. 428,161, now U.S. Pat. No. 5,196,311, issued Mar. 23, 1993. The contents of U.S. Serial No. 07/604,885 and U.S. Pat. No. 5,196,311 are hereby incorporated by reference into the subject application.

This invention was made with support under the National Institute of Health, National Heart Lung Blood Institute Grant No. HL 09902. Accordingly, the U.S. Government has certain rights in this invention.

FIELD OF THE INVENTION

This invention relates in general to a method of detecting homologous portions of a class of substances. More particularly, the invention provides an assay configuration which allows for reaction with a homologous portion common to all members of a class so as to detect the class members. Further provided is an assay configuration which allows for an additional reaction with a specific portion of one member of the class, so as to detect that specific member of the class.

BACKGROUND OF THE INVENTION

As various substances have come to be associated with disorders and diseases in human and animal species, a need for sensitive and specific detection methods for these substances has arisen. Electroimmunoassay (EIA) and radioimmunoassay (RIA) techniques evolved to provide important clinical diagnostic and research tools to detect such substances. Enzyme-linked immunosorbent assay (ELISA) techniques then developed to provide qualitative and quantitative assay methods which were more sensitive, specific, and reproducible.

Many substances sought to be detected are members of a class, in that the entire class shares a structural redundancy. Each individual member of the class may have a specific portion that is not shared with any other member of the class. For example, a protein may be present in many species. A class of antigens to this protein are present in multiple species, in that all members of the class of antigens share a homologous portion called a conserved epitope. However, the antigen in each particular species may have a portion which is different in each species.

In the development of detection methods for such classes, it may be desirable to detect all members of the class or the particular members of the class. For example, in the case of a class of antigens, one may wish to develop an assay that would detect the antigen in multiple species. In some instances, however, it may also be desirable to detect the antigen of a particular species.

For proteins, there is a tendency to assume that if an antibody to a particular protein's antigen of one species cross reacts with the same particular protein's antigen of another species, conserved epitopes (conserved across species lines or multi-species) for that antibody exist. One then assumes that an assay to detect that conserved epitope in multiple species can be devised. These assumptions are not valid for all proteins.

An example is the von Willebrand factor protein, where a review of the history of the protein shows the problem with these assumptions.

In 1926, Dr. Eric von Willebrand published the first description of the congenital human bleeding disorder that now bears his name. Similar congenital bleeding disorders were reported in swine by Hogan in 1941 and in dogs by Dodds in 1970.

It was not until the early 1960's that studies by Borchgrevink, Salzman and Bowie provided direct evidence for abnormal platelet function in von Willebrand Disease (vWD). Their work clearly suggested that a plasma protein which reacted with platelets and was required to control bleeding was absent or abnormal in individuals with vWD. Similar studies by Dodds in dogs supported the plasma nature of von Willebrand factor (vWf) and its essential role in reacting with platelets to control bleeding.

This plasma protein appeared related to factor VIII, the molecule deficient in patients with classic hemophilia A, because levels of factor VIII were also reduced in individuals with severe vWD. Scientific controversy persisted for close to a decade regarding the nature of the "antibleeding factor"deficiency in vWD, and whether it comprised the large carrier component of coagulation factor VIII or was a separate protein. A large body of biochemical evidence accumulated to support the notion that vWF was indeed the same protein that was deficient in hemophilia A. However, this was difficult to reconcile with the genetic evidence which demonstrated sex-linked inheritance for hemophilia and autosomal inheritance for vWD. Studies in the canine model of vWf by Dodds and co-workers provided further support for the hypothesis that the defective protein in vWD was not Factor VIII.

The controversy would continue undiminished until 1984 when the gene for Factor VIII was cloned. It became clear that Factor VIII was bound to another protein, vWf, which acted as a protective carrier protein for the Factor VIII molecule, prolonging its half-life in circulation. In the absence of vWf, plasma Factor VIII levels fell despite normal Factor VIII production at sites of synthesis.

In 1971 two major technical advances occurred which set the stage for an explosion of new research on vWf and vWD. The first was the development by Zimmerman of a specific precipitating antiserum in rabbits directed towards vWf which could be used to quantitate human vWf by the new method of rocket immunoelectrophoresis. The second was the work of Howard and Firkin on a functional test for human vWf using a drug called ristocetin, which reacted with vWf and platelets and caused them to agglutinate.

In parallel with studies on human vWf in the 1970's, studies were attempted in other species. Since highly conserved epitopes were expected at that time, a number of groups attempted to quantitate vWf in animal plasmas using the techniques of Zimmerman and Howard and Firkin. To the surprise and frustration of these groups, the methods proved unsuitable for detection of vWf in animal plasmas. This called into doubt the presence of functional epitopes for vWf conserved across species lines.

Specifically, vWf in common laboratory species like rat and rabbit could not be detected by either the immunological assay of Zimmerman or the functional assay of Howard and Firkin. In fact, Brinkhous et al. reported that a number of species were "ristocetin resistant", implying that a major functional conserved epitope for vWf was absent. Therefore, the earlier reports of general immunological reactivity, or cross species reactivity, as measured by Bennett and Ratnoff were called into question.

This led to demands for proper and specific negative controls to confirm that positive reactions in the various available assays were in fact reactions with vWf. The only other accurate means available to validate assays was through the use of vWf-deficient plasma, which limited the validated assays to human, porcine, or canine where vWf-deficient plasma was available.

In other species, serious investigators in the field resorted to the laborious task of purification of vWf from the species of interest in order to immunize goats or rabbits with it to produce polyclonal antibodies that would have the specificity and immunological properties required for use as precipitating antibodies in the Zimmerman assay. The Zimmerman method, however, was a very insensitive method. Furthermore, the need to purify vWf from a species of interest in order to assay for the same species vWf was not a practical solution for detecting vWf in multiple species, since each species required its own species-specific antibody.

As enzyme-linked immunosorbent assay (ELISA) technology replaced the rocket immunoelectrophoretic technique developed by Zimmerman in the mid 1980's for the quantification of human vWf, researchers such as Bradley reported their ELISA effectiveness using human antibody in monitoring vWf in non-human species. However, the non-human species were species previously known to cross react with human antibody to vWf from earlier assay techniques (such as porcine and canine). The published data of this work was restricted to these few species and, furthermore, did not provide evidence that adequate negative controls were used to establish the specificity for vWf in the animal plasma studied. Thus, broad multi-species cross reactivity was still in doubt based on the previous experiences of those skilled in the vWf art.

In 1987, the experts in the field of the NIH Hematology Study Section which reviewed grant applications criticized an application for research into a multi-species assay. This was based on the lack of ELISA technology for measuring canine vWf. The Study Section considered development of the appropriate technology (ELISA) essential to the success of such research. They did not believe this research could be accomplished because an ELISA for vWf with appropriate sensitivity did not exist. Their viewpoint was bolstered by existing knowledge at the time which revealed the difficulties encountered when using human based vWf assays with animal species. They did not expect that the insensitive Zimmerman vWf technique would work in multiple species, let alone an ELISA based assay.

It is likely that the review committee was aware of the difficulties encountered with earlier assays for vWf when the species of interest was not human, and did not expect that a multi-species ELISA could be developed.

Thus, the need for a detection method for von Willebrand factor in multiple species continues to exist. There are many substances similar to von Willebrand factor in which a class of substances is thought to exist, but for which a detection method for the entire class has yet to be developed. Such substances include, for example, coagulation factor VIII, reproductive hormones, acute phase proteins, tumor markers, rheumatoid factors, cytokines, and various drugs and toxins.

A method of detecting such classes of substances with accuracy and sensitivity is needed for both research and clinical diagnostic purposes.

SUMMARY OF THE INVENTION

This need is met by the detection method according to the subject invention. The members of the class according to the invention have a common structural redundancy, and are chemically or biochemically consistent throughout the class. The configuration of the detection method allows for capture of the class (using polyclonal or monoclonal antibodies or other capture reactants that have the ability to recognize and tightly bind the class members) based on the capture reactants' ability to interact with conserved regions or epitopes within a class or family of structurally related compounds (they could be proteins, alkaloids, toxins, surface receptors, hormones, drugs, etc.). Once captured, the compounds can be detected by a second reactant (i.e. a monoclonal antibody or polyclonal antibody), which could be capable of recognizing specific epitopes present on the analyte of interest (a specific class member) or another conserved portion on all class members. Each of these sites is available or becomes available when the class members are bound to the capture reactant.

This assay configuration resembles a double-sandwich ELISA assay. Although double sandwich ELISAs are known, this claimed assay configuration reveals specific epitopes or conserved epitopes that were normally not available by capturing the antigen on the microtiter plate. These specific and conserved epitopes would not normally be available if the antigen were coated directly onto a microtiter plate (without a capture antibody), or if the antigen were reacted directly with non-immobilized antibody.

The resulting complex is then detected by interaction with a reporter molecule (i.e., alkaline phosphatase, biotin-avidin, horseradish peroxidase, a radioisotope, dyes, fluorescent signals) coupled directly or indirectly to the second reactant called the sandwich antibody.

By putting the reactants in a captured format where all extraneous material is washed away, non-specificity of reactions is eliminated. Therefore, subtle changes in the reactants can be detected leading to increased sensitivity of the assay.

In one example, the ELISA assay configuration of the subject invention allows for the detection of von Willebrand factor with high sensitivity and specificity in a variety of species that could not previously be analyzed in a single assay format. This is accomplished due to the assay configuration which utilizes an antibody capable of reacting with conserved epitopes of the vWf antigen, present in a configuration which allows the antibody to recognize the conserved epitopes. If the antibody is not present in the right configuration, which is provided by the subject invention, even if it is capable of recognizing the conserved epitope it will not do so.

The importance of the assay configuration can be understood by looking at the von Willibrand factor protein, which is a very large glycoprotein. It has a structure which is three dimensional and also has subunits. There are epitopes within the molecule that are highly conserved across species lines. The folding property of the molecule as species lines are crossed, however, will be different because the primary sequence will be different. The configuration of the protein when it is folded up on itself may therefore be different so that an epitope that is highly conserved may not be available for reaction in a liquid phase because it is internalized.

The assay configuration of the subject invention immobilizes the vWf protein with a capture antibody, resulting in a structuring of the vWf antigen in such a way as to make available the binding sites for the sandwich antibody. The reaction of the vWf Ag with the immobilized capture antibody reveals conserved epitopes which the sandwich antibody can react with. The assay configuration is highly sensitive and specific because it allows access to the highly conserved epitope. It is not sufficient to just have the epitope present, as in previous assay configurations. The conserved epitope must be available for reaction with the antibody.

The assay configuration will also work with other proteins that demonstrate immunologic properties of only limited cross-species reactivity to antibodies expected to be more widely cross reactive, and therefore permits detection of heretofore unrecognized conserved epitopes.

Generally, the method is directed to the detection of an analyte in a sample. The analyte according to the invention is a member of a class of substances. The class of substances is defined by each of the class members having a homologous portion in common with all other members of the class. For example, the class of substances may comprise an antigen such as von Willebrand factor antigen (vWF Ag). Each member of the class, i.e. each vWF Ag, has a homologous portion referred to as a conserved epitope which is common to all members of the class. vWF Ag from human, canine, porcine, bovine, guinea pig, horse; cat, monkey, sheep, rat, mouse, goat, rabbit, manatee, llama, and-camel have this homologous portion in common. The analyte is a member of the class, i.e. canine vWF Ag. The analyte, i.e. canine vWF Ag, also has a specific portion present only on that analyte. In the example given, the canine vWF Ag has a specific portion present only on the canine vWF Ag, and not present on the horse or human or porcine, etc. members of the class.

The invention provides a method of detecting a particular analyte, i.e. canine vWF Ag, in a sample. The method utilizes an assay configuration which allows detection of this homologous portion to identify members of the class, and then detection of the specific portion so as to identify the particular analyte. This improves sensitivity of the detection method.

Specifically, a particular analyte is chosen for analysis, such as canine vWF Ag. First, the members of the class to which the analyte belongs are captured in the assay configuration as follows. A first substance capable of reacting with the homologous portion of the class is attached to an immunological reaction surface. In the vWF Ag example, the first substance may comprise a polyclonal antibody to vWF Ag. The attached first substance is then reacted with a sample to be analyzed for analyte, so as to react with and bind homologous portions of any members of the class present in the sample, i.e. any vWF Ag.

According to this embodiment of the invention, such reaction and binding reveals a previously undetectable and unreactable binding site for the specific portion of the particular analyte being analyzed, i.e. canine vWF Ag. The bound class members, bound due to their homologous portions, are then reacted with a second substance (such as an antibody) capable of reacting with the revealed binding site for the specific portion of the analyte. The reaction and binding of the second substance to the specific portion is then detected. This detection of the specific portion is thus a detection of analyte present in the sample. If no analyte was present in the sample, then no binding site for the specific portion would have been revealed and no binding of the second substance would occur.

This embodiment thus provides a method of detecting an analyte in a sample, where the analyte is a member of a class of substances having a homologous portion in common with all other members of the class and a specific portion present only on the analyte.

The example given is vWF Ag as a class of substances, with canine vWF Ag as the analyte of interest, utilizing antibodies as the first and second substances. The invention is equally applicable to other analyte/classes known to those skilled in the art, where advantage can be taken of a homologous portion to increase the sensitivity of an assay for a class or an analyte of interest. For example, other antigens with homologous portions can be utilized, or various blood factors which exist as a class'can also be utilized. Coagulation Factor VIII is one example of a blood factor having homologous portions common to all members of the Factor VIII class of substances, while Factor VIII from particular species have specific portions common only to that particular species. The assay configuration described in the context of vWF Ag can also be utilized to bind the homologous portion of any members of the Factor VIII class to a first substance, revealing a binding site for the particular specific portion of the Factor VIII analyte, in canine Factor VIII. A second substance can then be reacted with and bound to the revealed binding site, and then detected so as to detect the particular Factor VIII analyte,. i.e. canine Factor VIII.

The class of substances could also be various proteins, alkaloids, toxins, surface receptors, hormones, drugs and'cytokines.

In a further embodiment of the subject invention, the assay configuration can be utilized to detect members of the class, without continuing on to detect particular analytes. In this embodiment, for example, all members of a class are detected without specifically identifying the particular members as follows. The class of substances of interest are selected. As in the previous embodiment, all members of the class have a homologous portion in common with all other members of the class. A substance capable of reacting with the homologous portion is attached to an immunological reaction surface. This attachment reveals a previously undetectable and unreactable binding site for the homologous portion. The attached substance is then reacted with a sample to be analyzed for the class of substances. The revealed binding site on the attached substance then reacts with and binds to any homologous portions of the class present within the sample. The bound class members can then be detected which were present in the sample. If no class members were present in the sample, then no binding would occur to the revealed binding site for the homologous portion.

BRIEF DESCRIPTION OF THE FIGURES

These and other objects, features and advantages of this invention will be evident from the following detailed description of preferred embodiments when read in conjunction with the accompanying drawings in which.

DETAILED DESCRIPTION OF THE INVENTION

Figure 1:
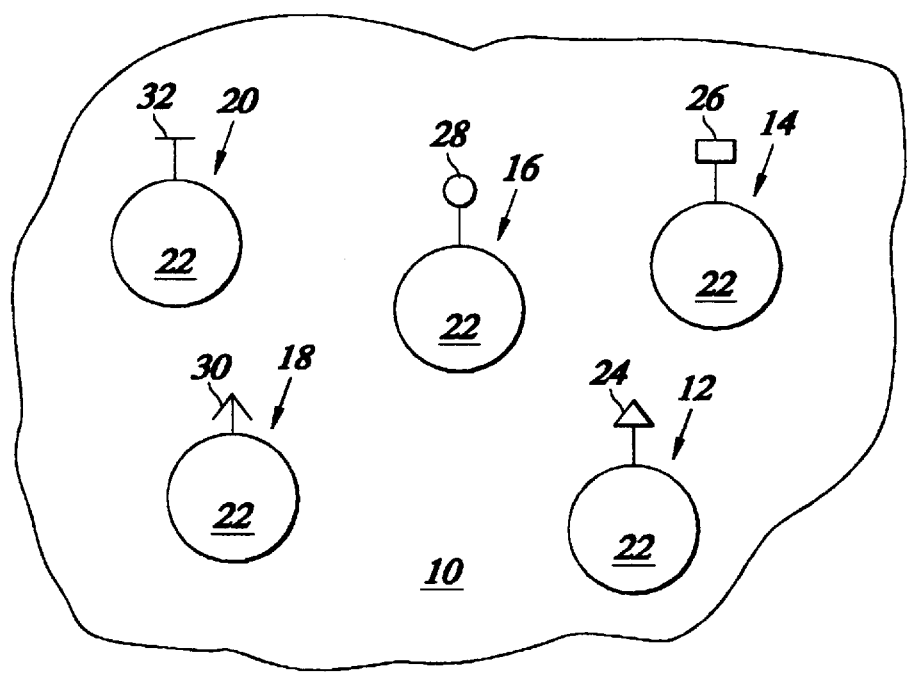
FIG. 1 is a representation of a class of substances with an analyte of interest.

The methods of the subject invention are used to detect members of a class of substances, or to detect an analyte of interest which is a member of such a class. As shown in FIG. 1, the class of substances 10 includes members 12, 14, 16, 18 and 20. Each member of the class has a homologous portion 22 common to all members of the class. Each member also has a specific portion present only on that particular member. Member 12 has specific portion 24; member 14 has specific portion 26; member 16 has specific portion 28; member 18 has specific portion 30; and member 20 has specific-portion 32.

Figure 2:
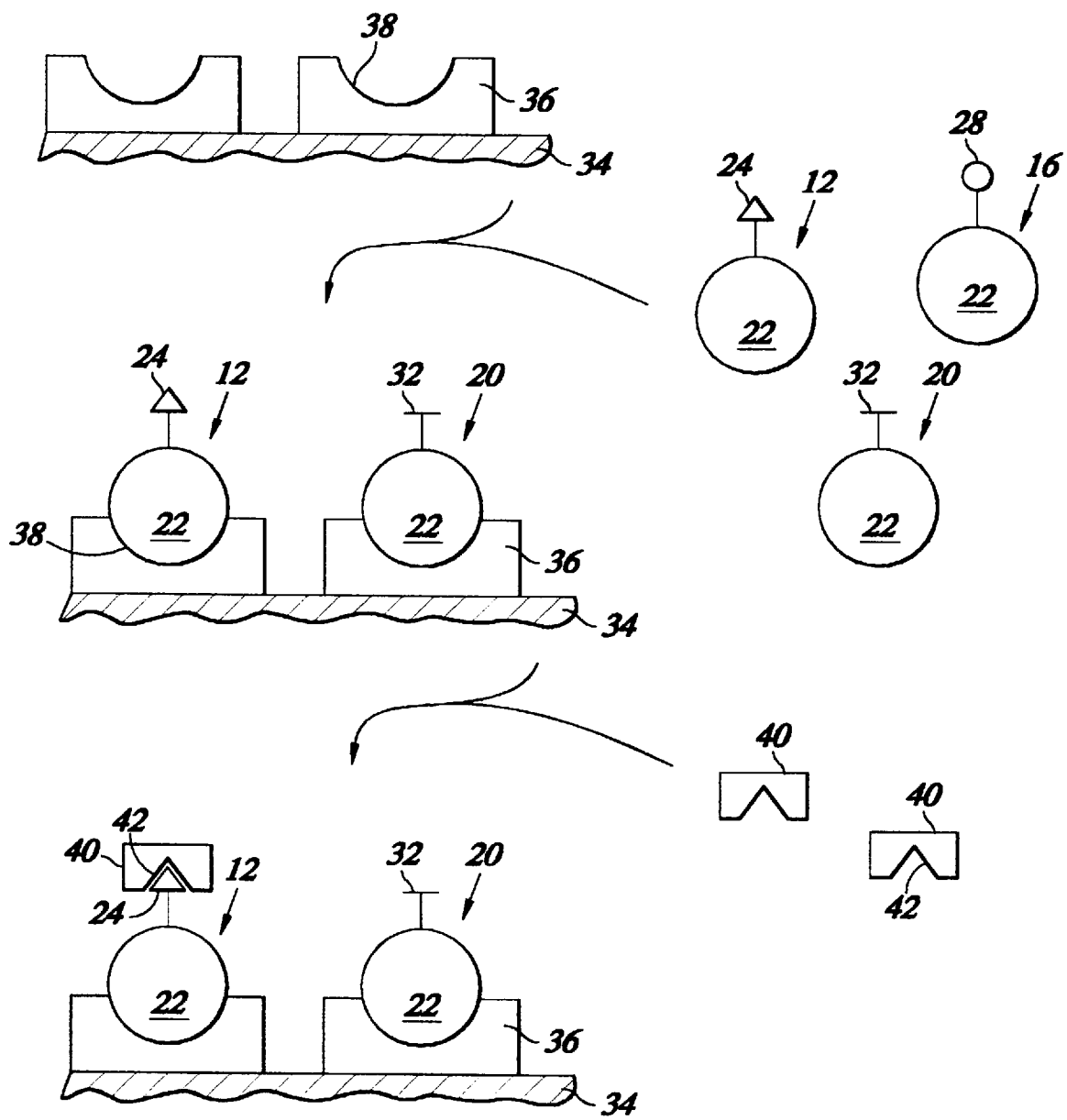
FIG. 2 illustrates the method of detecting the analyte of interest shown in FIG. 1 according to one embodiment of the subject invention.

Referring to FIG. 2, the method of detecting an analyte of interest, member 12, is depicted. Initially, a first substance 36 is attached to an immunological reaction surface 34. The first substance 36 is capable of reacting with the homologous portion 22 of the class of substances 10, due to the presence of a binding site 38 for the homologous portion 22. The attached first substance is then reacted with a sample to be analyzed for the analyte of interest, member 12. The sample as shown contains members 12, 16, and 20.

The reaction results in the binding of the homologous portions 22 in the sample (only the binding of members 12 and 20 are shown) to the binding site 38 of the first substance 36. This reaction and binding reveals the previously undetectable and unreactable binding site of the specific portion, 24 or 32, of the class members. A second substance 40 is then reacted with the resulting structure. The second substance 40 has a binding site 42 for the specific portion 24 of the analyte of interest, member 12.

After the second substance 40 has bound to the specific portion 24 of the member 12, the bound second substance is detected. As such, the presence of the analyte of interest, member 12, in the sample is detected. The assay configuration according to this embodiment revealed the binding site 42 so that the member 12 could be bound and detected.

Figure 3:
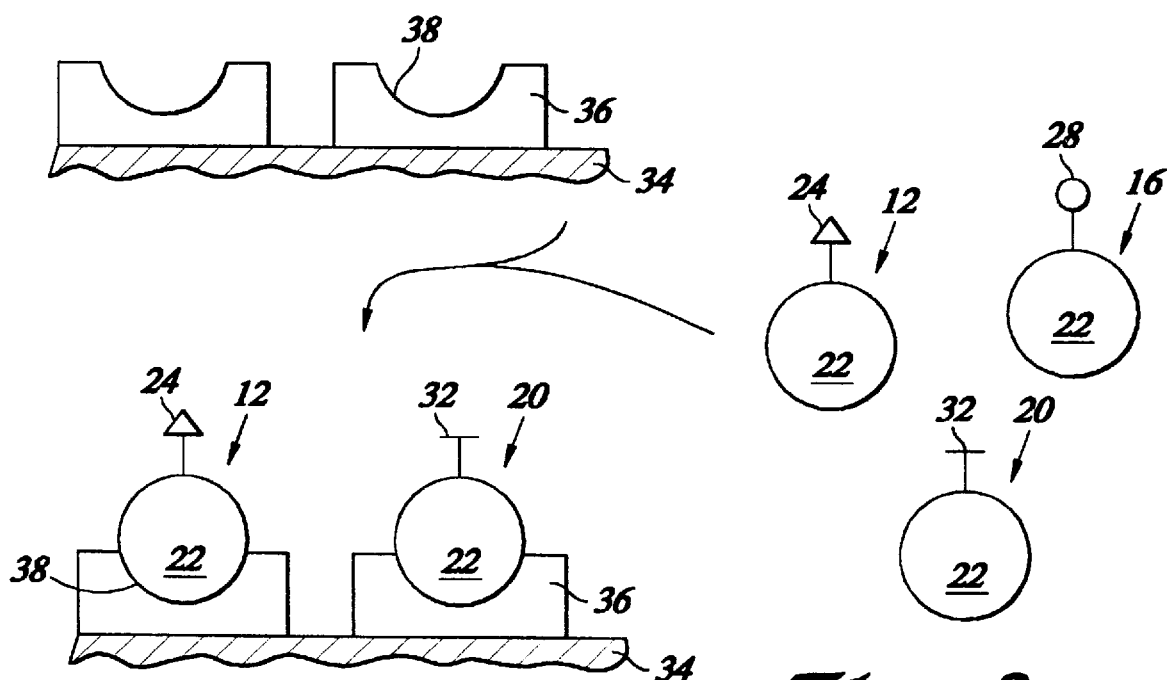
FIG. 3 illustrates the method of detecting members of the class of substances shown in FIG. 1 according to another embodiment of the subject invention.

Referring to FIG. 3, the method of the subject invention can also be utilized to detect the members of a class of substances. In this embodiment, the first substance 36 is again attached to an immunological reaction surface 34. The attachment of the first substance 36 reveals the binding site 38 for the homologous portions 22 of the class members. The attached substance 36 is then reacted with a sample, which as shown contains members 12, 16 and 20, so as to bind the homologous portions 22. The members of the class which were present in the sample can then be detected by detecting the bound members.

The assay configuration according to this embodiment revealed the binding site 38 so that the class members could be bound and detected.

Having described the methods of the subject invention, they will be more readily understood in the context of specific classes and analytes of interest as disclosed in the following examples.

These examples illustrate a reaction and binding construct which structurally makes available a binding site of a specific portion of an analyte such that a first substance relates, for instance positional, to the analyte to be detected so as to permit a binding site of the analyte which is normally unavailable, to become available for binding and detection when immobilized.

EXAMPLE 1
Von Willebrands Factor

The development of ELISA for vWf required an exhaustive series of experiments with ELISA formats, antibody sources (for example, goat, rabbit, monoclonal), adsorbtion steps, washing procedures, visualization protocols, and actual configuration of sandwich and capture antibodies to make the ELISA operative for detection of very low levels of vWf in human, canine, and a list of other species.

In a first embodiment of the subject invention, the antibody which recognizes an evolutionarily conserved epitope is a polyclonal antibody raised in a vertebrate species, preferably rabbits or goats. The polyclonal antibody is raised in response to vWf:Ag from canines and is also referred to as anti-canine von Willebrand factor antigen (anti-canine vWf:Ag). The polyclonal antibody is used in an assay which is one embodiment of the subject invention, a modified double sandwich ELISA assay, to qualitatively and quantitatively detect von Willebrand factor in a variety of vertebrate species.

In additional embodiments of the subject invention, the antibody which recognizes an evolutionarily conserved epitope is a polyclonal antibody raised in one of several vertebrate species, or a monoclonal antibody. The antibodies are raised in response to vWf:Ag from a variety of vertebrate species in addition to canines. The antibodies are used in an assay which is one embodiment of the subject invention, a modified double sandwich ELISA assay, to qualitatively and quantitatively detect von Willebrand factor in a variety of vertebrate species. The antibodies are used in an assay which allows the antibody to recognize the evolutionarily conserved epitopes of von Willebrand factor antigen, and results in an assay which allows the qualitative and quantitative detection of von Willebrand factor antigen in numerous vertebrate species.

Initially, in the first embodiment, purified canine vWf:Ag is utilized to raise antibodies to canine vWf:Ag (hereinafter, anticanine vWf:Ag) in selected vertebrate species such as rabbits or goats. These antibodies have been routinely obtained following the immunization and screening procedures disclosed herein. The antibodies have been produced in five separate rabbits and have been prepared from those rabbits following at least twenty separate bleedings. The resulting antibodies from all five rabbits were suitable for use in the ELISA.

These antibodies are obtained by utilizing standard checkerboard screening techniques in which various antibodies are tested for use as capture/sandwich/detector antibodies in the assay configuration. The suitable antibodies are those that have broad multi-species reactivity, have low background effects, and are linearly quantitative across a wide range of antigen concentrations. Given the assay configuration, one skilled in the art can take an antibody and evaluate its suitability for the configuration using known techniques.

The surface of a reaction vessel, preferably the well of a microtiter plate, is then coated with the anticanine vWf:Ag to serve as the capture, immobilizing or anchor antibody. Test plasma containing an unknown quantity of vWf:Ag is then added to the test vessel. A second anticanine vWf:Ag is added to the reaction vessel. This is the sandwich antibody and should be different from the capture antibody, i.e. raised in a different species. For example, if the capture antibody is raised in a rabbit, the sandwich antibody may be raised in a goat, or vice versa.

A detectant for the sandwich antibody, for example, an enzyme-conjugated anti IgG, is then added to the reaction vessel. This reagent should be reactive with the sandwich antibody (i.e. raised against the same species), but not reactive with the capture antibody. For example, it should be anti-goat IgG if the sandwich antibody was raised in a goat.

The amount of vWf:Ag in the unknown plasma is then detected by measuring the amount of antibody-conjugated detectant. For example, if the detectant is an enzyme which produces a color reaction, the intensity of the color, i.e. the optical density of the color produced, can be utilized to determine the amount of vWf:Ag in the unknown either qualitatively or quantitatively.

This embodiment is a modified ELISA procedure. Those skilled in the art will recognize that the generalized outline omits certain of the specific steps such as serial dilution and washing with appropriate buffers which are standard in the ELISA procedure. Although specific buffers and other reagents will be described hereinafter, and specific dilutions will be employed to illustrate the invention, the skilled artisan will recognize that these are illustrative only and that many equivalents are possible.

The specificity of this assay relates to the assay configuration in which the capture and sandwich antibodies are raised in different species, thus resulting in a detector antibody which is not raised in the same species as the capture antibody and therefore detects only the sandwich antibody in the assay. The ability of the assay to detect vWf resides in the reaction of the sandwich antibody with available epitopes on the vWf antigen, revealed by the vWf antigen's binding to the capture antibody.

The operation of this invention, especially in the qualitative (i.e. screening) mode requires the selection of a standard vWf:Ag concentration to which one or more concentrations of known standards and the plasma, the concentration of which is to be determined, will be compared. The standard may be prepared as described below.

A convenient single standard is 65% (0.65 unit/ml) of the plasma vWf:Ag level of healthy individuals (hereinafter called normal plasma and assigned a value of 100% or 1 u/ml), which may be selected for purposes of comparison with other plasmas. The assay can be made semiquantitative or quantitative by selecting several reference standards having vWf:Ag levels such as 15% (0.15 u/ml), 35% (0.35 u/ml), and 65% (0.65 u/ml) of normal. These levels are selected for the presently preferred practice of the invention because extensive experience with EIA testing of healthy individuals of several species has indicated that the lower limit for the normal range is about 60% (0.6 u/ml). A person or animal is statistically at low risk for bleeding during surgery or other stress situations and is unlikely to transmit vWd to progeny if the level of vWf:Ag is at least 60% (0.6 u/ml). Individuals with levels of less than 60% (0.6 u/ml) require special caution. The methods of this invention are useful in genetic surveillance in a breeding program to reduce or eliminate the prevalence of vWd in various animal species such as dogs, cats, horses, nonhuman primates, and other domestic, laboratory or exotic animals.

In a qualitative ELISA procedure according to the subject invention, test strips (e.g. Duo-Strips containing eight wells available from Dynatech Corporation, Alexandria, Va.) are coated with 100 $\mu$l/well of capture (e.g. rabbit) antibody to canine vWf:Ag appropriately diluted (e.g. 1:500) with coating buffer. Coating is usually completed for many strips at once. The strips are stacked and incubated overnight in a humid 37° C. incubator. The top strips are covered by tape. The following day, the plates are washed 3 times with PBS-Tween buffer, 200 $\mu$l in each well.

150 $\mu$l of after coating (saline-albumin) buffer is added to each well and incubated 1 hour at room temperature or at 4° C. and stored for up to two months, when the strips are tape-sealed. Immediately prior to the addition of plasma dilutions, the strips are washed three fold with PBS-Tween as above.

The single standard pooled plasma, which has been prepared to contain 65% (0.65 u/ml) vWf:Ag, or several standards prepared to contain 15% (0.15 u/ml), 35% (0.35 u/ml) as well as 65% (0.65 u/ml) vWf:Ag, are diluted 1:100 in dilution buffer. The normal and abnormal control plasmas and unknown samples are also diluted 1:100. The normal plasma serves as a control to monitor the system. The abnormal control is 0% vWf:Ag.

100 $\mu$l of the 15% (0.15 u/ml), 35% (0.35 u/ml) and/or 65% (0.65 u/ml) standard plasma dilutions are added to the first, third, and fifth wells either in series or in replicate strips. 100 $\mu$l of the diluted unknown plasma is added to the second, fourth, and sixth wells. 100 $\mu$l of the normal control is added to the seventh well and 100 $\mu$l of the abnormal control is added to the eighth well. When the plasma dilutions are complete, the plate is sealed with tape and incubated for one hour at room temperature in the dark. The plasma dilutions are then washed from the wells three times with 200 $\mu$l of PBS-Tween.

Following the washing with PBS-Tween, 100 $\mu$l of second (e.g. goat) anticanine vWf:Ag appropriately diluted (e.g. 1:250) in dilution buffer is added to each well and the sealing tape is replaced. The strip is incubated for one hour at room temperature in the dark. Then the strips are washed three times with PBS-Tween as above.

Following the wash, 100 $\mu$l well of peroxidase-conjugated antibody (e.g. porcine anti-goat IgG) appropriately diluted (e.g. 1:10000) in dilution buffer is added. The sealing tape is replaced and the strip is incubated at room temperature for one hour in the dark. The plate is then washed three times with PBS-Tween as above. Using an aerosol can the strip is sprayed with citrate buffer three times and is shaken to drain its washings into a sink. Following the spray step, 100 $\mu$l of the OPD-$H_2O_2$ solution is added to each well. After approximately 10 minutes the reaction is terminated by adding 100 $\mu$l/well of 4.5M $H_2SO_4$.

Under standard indoor fluorescent lighting, the well strips are placed over a white background (3×5 inch card works well) and compared for the color intensity of the three wells containing the 65% (0.65 u/ml) vWf:Ag standard or the series of 15% (0.15 u/ml), 35% (0.35 u/ml), and 65% (0.65 u/ml) standards to the unknown samples which are in alternate wells in triplicate. The objective of the comparison is to determine if the unknowns are of more, less, or of equal color intensity than the standards. The normal control plasma is assigned 100% (1 u/ml) vWf:Ag and should be obviously of greater color intensity that the 15%, 35% or 65% standards while the abnormal control plasma known to be genetically homozygous deficient in vWf has less than 0.002% ($0.2\times10^{-4}$ u/ml) vWf:Ag and should have no color.

The strip may be read with an ELISA reader at 490 nm with the abnormal control plasma serving as the blank. Comparison of the quantitative optical densities of the triplicate or serial standards and the triplicate unknown sample virtually eliminates any uncertainty of visual comparisons and permits definitive quantitation of the unknown vWf:Ag level.

The color intensity of the unknown is graded as being stronger than, equal to or of lesser color intensity than the standards. Experience with a very large number of such qualitative tests has made it clear that visual comparison readily defines three or more groups of unknown plasma vWf:Ag levels; e.g. below 20% (0.2 u/ml), 30–40% (0.3–0.4 u/ml), 60–75% (0.60–75 u/ml), and greater than 80% (0.8 u/ml).

Using these screening determinations, the clinician or animal breeder can quickly determine if a sample has plasma levels less than or greater than 70–75% (0.7–0.75 u/ml) vWf:Ag. Patients with vWf:Ag levels above 75% are at little or no risk for surgical or other bleeding caused by reduced levels of vWf:Ag or are unlikely to transmit vWd to their offspring.

Plasma from individuals that generate virtually no color reaction are affected with vWd.

A quantitative ELISA procedure is also provided, which utilizes the EL 312 ELISA Plate Reader available from Bio-Tek Instruments, Winooski, Vt. However, the procedure is not limited to this specific instrument, as will be evident to those skilled in the art.

Microtiter plates with 96 wells (e.g. 96 plate Immulon I, Dynatech Corporation) are coated with 100 $\mu$l/well of rabbit anticanine vWf:Ag (the DEAE purified fractions prepared as described above) appropriately diluted (e.g. 1:500) with coating buffer. Fifteen plates are usually coated at once. The plates are stacked and incubated overnight in a humid 37° C. incubator. The top plate is covered by an empty plate. The following day, the plates are washed 3 times with PBS-Tween buffer.

200 $\mu$l of freshly prepared after-coating buffer is added to each well and incubated 1 hour at room temperature, or at 4° C. for up to two months when the plates are tape-sealed.

A pooled plasma from healthy individuals of the species being tested is diluted to create a series of standards [100% (1.0 u/ml), 50% (0.5 u/ml), 25% (0.25 u/ml), 12.5% (0.125 u/ml), and 6.25% (0.0625 u/ml)] to which the unknown sample plasmas will be compared. Six or more tubes are prepared and designated as standards (labelled $STD_1$, $STD_2$, $STD_3$, $STD_4$, and $STD_5$ and a blank is prepared. To the $STD_1$ add 10.0 ml of dilution buffer, to the other standards add 1.0 ml (1000 $\mu$l) of dilution buffer. 50 microliters ($\mu$l) of the 100% standard is added to 10.0 ml of the dilution buffer in $STD_1$ tube and the tube is capped with Parafilm (3M Corporation) and inverted gently six times—this is a 1:200 dilution. Next, 1000 $\mu$l of the 1:200 dilution is added to 1000 $\mu$l of dilution buffer in the $STD_2$ tube which equals a 1:400 dilution. With a pipetting device mix the $STD_2$ six times and then add 1000 $\mu$l of the mixed $STD_2$ to the $STD_3$ tube and mix as above. Add 1000 $\mu$l of the $STD_3$ tube to the $STD_4$ tube and mix; add 1000 $\mu$l of $STD_4$ to the $STD_5$ tube and mix. Add 1 ml of dilution buffer to the blank tube.

One dilution tube for each unknown sample is prepared with buffer before the plasma is pipetted. The tube labeled 1:600 has 12 ml of buffer. The dilution tubes are lined up behind the plasma samples in the test tube rack.

Using a fresh pipette tip for each unknown plasma sample, 20 $\mu$l of the plasma sample is added to the 12 ml (1:600 dilution) and capped with fresh Parafilm and inverted six times Each unknown plasma sample is similarly diluted. An internal control (reference) plasma of known vWf:Ag level can also be used and diluted similarly. Samples with low and/or no detectable vWf:Ag should also be included on the plate as abnormal controls to assure the specificity, validity, and accuracy of the test.

Immediately prior to the addition of plasma dilutions to the plates, the wells are washed three times with PBS-Tween, 200 $\mu$l/well. 100 $\mu$l of each sample is added per well. Dilutions are run in triplicate for each standard. The unknowns are run in triplicate and are distributed on the plate as in the Master Chart shown in Table I. The additions are planned in advance and the Chart is used as a guide. When the plasma additions are complete, the plate is sealed with tape or otherwise covered and stored at 4° C. overnight.

The Master Chart shown in Table I gives the results of an actual test with canine plasma. In the Master Chart, boxes 1–24 are samples to be tested. The boxes marked '83' contain the internal reference plasma having a known value of 83% (0.83 u/ml) vWf:Ag. 'Blk' is the buffer blank. The boxes marked "Std" are the standard plasma dilutions. The boxes marked "Sple" are the unknown sample plasmas. "AC" is the abnormal control (homozygous vWf:Ag deficient plasma).

The plasma dilutions are then drained from the wells which are then washed three times with PBS-Tween after the overnight step and between each antibody incubation. Following the washing with PBS-Tween, add to each well 100 $\mu$l of second (e.g. goat) anticanine vWf:Ag appropriately diluted (e.g. 1:1000) in dilution buffer and replace the sealing tape or cover. Incubate for one hour at room temperature in the dark, then wash three times with PBS-Tween as above.

Add 100 $\mu$l/well of peroxidase-conjugated antibody (e.g. porcine anti-goat IgG) appropriately diluted (e.g. 1:10000) in dilution buffer. Replace the sealing tape or cover and incubate at room temperature for one hour in the dark. Then wash three times again with PBS-Tween as above.

Using an aerosol can, spray the plate (6–10inches away) with citrate buffer three times and vigorously shake the plate's washings into a sink after each spray. Following the spray step, 100 $\mu$l of the $OPD-H_2O_2$ substrate is added to each well with a multichannel pipetting device and fresh tips. After approximately 10 minutes, the reaction is terminated by adding 100 $\mu$l/well of the 4.5M $H_2SO_4$. The pipette tips do not need to be changed between the OPD and $H_2SO_4$.

The top of the plate is wiped dry with a lint-free pad and inserted in an ELISA plate reader and a report form with final results is generated. These results are summarized on-the Master Chart (see Table I).

An examination of the chart is convincing of the accuracy of the test as shown by the low deviations in the readings listed in different boxes for the same compositions. Compare, for example $STD_1$ in boxes A-1, A-12 and H-12, or 83 REF in boxes A-7 and H-6.

The optical densities are converted to percent vWf:Ag by comparison with the quadratic curve generated from the triplicate values of the five standards using a soft ware package from the instrument manufacturer.

The Master Chart consolidates all of the above information including sample numbers, machine readings and percent of vWf:Ag per standard, reference or sample.

The specificity, accuracy and reproducibility of the process of this invention will be readily apparent from inspection of the Master Chart.

The modified double-sandwich ELISA developed for canine von Willebrand factor also cross-reacts with plasma von Willebrand factor of other mammalian species and can be used to quantitate von Willebrand factor in at least 12 other species. Specificity of the assay was demonstrated using vWd plasma from pigs, humans, and a horse. Agarose filtration fractions of cat, rat, and guinea pig plasma when analyzed by ELISA had the reactive antigen in the void volume, which coincided with the typical multimeric pattern for von Willebrand factor. Significant cross-species reactivity was observed between monoclonal antibodies (Mabs) against porcine and bovine von Willebrand factor and plasmas from 12 species. Mixed combinations of Mabs and various polyclonal antibodies to vWf:Ag were used to quantitate vWf:Ag in pig, horse, dog, human, and mouse plasmas. Using Mabs that capture rabbit vWf:Ag and goat antidog vWf:Ag as the sandwich antibody, a quantitative assay for rabbit vWf:Ag was constructed. The same sandwich and conjugate antibody were also used to visualize rabbit von Willebrand factor multimers. These findings permit, for the first time, the measurement of vWf:Ag in a variety of vertebrates for which species-specific immunological reagents are not available.

One embodiment of the subject invention is directed to a modified double-sandwich ELISA for canine vWf:Ag which is cross-reactive with the plasmas of at least 12 other mammalian species and can be used to construct sensitive quantitative assays for vWf:Ag in these species. Significant species cross-reactivity was also observed between Mabs and the vWf:Ag of various species. When the Mabs were used in combination with polyclonal antibodies they could also be used to quantitate vWf:Ag.

In this multi-species assay, blood from 14 different mammalian, species, including humans and dogs, was collected into 1/10 volume of 3.8% sodium citrate dihydrate and centrifuged twice (18,000×g) to render the plasma platelet free. Samples were stored in aliquots at −20° or −40° C. A single plasma sample was obtained from a monkey and manatee, and pooled plasmas (n=6) were prepared from rabbits, rats, guinea pigs, cats, goats, sheep, cows, horses, mice, dogs, pigs, and humans. vWd plasmas from dogs, pigs and a horse were used to confirm specificity of the assays. The porcine vWd plasma was kindly supplied by Dr. Walter Bowie of the Mayo Clinic, Rochester, Minn. Human plasmas (BR, DW, SF) were made cell-free, as above, from the citrated blood of laboratory staff. The human blood samples were drawn after informed consent had been obtained under an approved protocol from the Institutional Review Board of the New York State Department of Health and according to the Principles of the Declaration of Helsinki. The vWf:Ag-depleted human plasma (AC) was purchased from BioData Corp. (Horsham, Pa.).

Ten ml of pooled plasma from laboratory rats, guinea pigs, rabbits, or domestic short-haired cats was filtered at room temperature with phosphate-buffered saline, pH 7.4, at 20 ml per hour over a 2.5×45-cm 6% agarose (Bio-Gel A5M, Bio-Rad, Rockville Centre, N.Y.) column. The absorbance of the 5-ml fractions was monitored at 280 nm. As collected, each fraction was stored at 4° C. and after completion of the chromatography, was divided into 0.5-ml aliquots and stored at −50° C. The fractions were subsequently assayed for vWf:Ag and for the presence of von Willebrand factor multimers as previously described.

Antibodies to canine vWf:Ag were prepared in a rabbit and a goat. The immune sera were adsorbed twice with cryoprecipitate from the plasma of a dog homozygous for type III vWd (see above). IgG was prepared from the goat and rabbit sera and was stored at −50° C. The same purified vWf:Ag preparation used to immunize the goat was used to immunize four Balb/C mice. Pre-fusion mouse serum samples were pooled and used as a sandwich antibody. Six ascitic-fluid Mabs against bovine vWf:Ag (No.'s 1,2,6,7, 16&10) were kindly supplied by Dr. Edward Kirby of Temple University, Philadelphia, Pa. Seven-Mabs against porcine vWf:Ag were kindly supplied by Dr. David Fass of the Mayo Clinic, Rochester, Minn. and were in IgG form (W1-1, W1-2, W1-5) or ascitic fluid (W1-3, W1-4, W1-8, W1-16). Rabbit antiporcine vWf:Ag was supplied by Dr. Bowie. Commercially purchased antibodies were rabbit antihuman vWf:Ag supplied by DAKO, Carpenteria, Calif., and pig anti-goat IgG-conjugated to horseradish peroxidase, goat anti-mouse IgG-horseradish peroxidase and goat anti-rabbit IgG-horseradish peroxidase, each supplied by TAGO, Inc., Burlingame, Calif.

Immulon I microtiter plates (Dynatech, Alexandria, Va.) were coated with various antibodies by dilution in a coating buffer and dispensing 100 μl of the solution into each well of the microtiter plate, covering the plate and incubating it overnight in a moist 37° C. chamber. The following morning the wells were flushed three times with washing buffer, and 200 μl of blocking buffer was stored in the wells (at least overnight) at 4° C. until the plate was used. Plates stored at 4° C. with blocking buffer were reactive for at least three months. Plates were coated with the rabbit antidog vWf:Ag IgG at a 1:500 dilution or rabbit antihuman vWf:Ag IgG at a 1:4000 dilution or rabbit antiporcine vwf:Ag at 1:1000 dilution. The antiporcine and antibovine vWf:Ag Mabs were utilized as coating antibodies at a 1:100 dilution.

Coated plates were flushed with 100 μl of washing buffer three times and then 100 μl of the appropriate dilution of plasma was loaded into the wells and incubated for one hour at room temperature. The plates were flushed as above and 100 μl of the diluted sandwich antibody was added to the wells, incubated for one hour and flushed. 100 μl of the conjugated antibody diluted 1:10,000 was added to each well for an additional one hour incubation. Following a final PBS-Tween wash, conjugated antibodies were sprayed with citrate buffer three times before the addition of the o-phenylenediamine dihydrochloride substrate. The substrate color change was halted after 5–20 minutes with $H_2SO_4$. Plates were scanned at 490 nm with a Bio-Tek EL312 microplate reader (Bio-Tek, Winooski, Vt.). Standard curves were constructed and sample concentrations were determined with the BIO-TEK Kinicalc software program, which plotted the logarithm of the optical density versus the logarithm of the concentration and employed a quadratic curve fit.

When an antibody combination of rabbit antidog vWf:Ag as capture reagent and goat antidog vWf:Ag as sandwich antibody, at 1:10 and 1:100 dilutions was used, plasmas from 10 species studied exhibited moderate to strong reactivity. Cow and mouse plasmas showed weaker reactions, which were substantially above the blanks. Rabbit plasma was unreactive using this antibody configuration. When the sandwich antibody concentration was decreased to 1:1000, the dog, cat, sheep and goat plasmas continued to strongly react. Human plasma also strongly reacted in this ELISA. The absorbance data in Table II demonstrate the relative cross-reactivities of various animal plasmas using polyclonal capture and sandwich antibodies to canine von Willebrand factor.

The absorbances of type III vWd plasmas from pigs and dogs, and vwf:Ag-depleted human plasma at the 1:100 dilution did not generate absorbances above the buffer blank in this ELISA. When type I vWd plasmas of pigs and humans were quantitated in the canine-specific ELISA, the vwf:Ag levels were comparable to the results of ELISAs with species-specific antibodies (Table III).

When cat, guinea pig, and rat plasmas were fractionated on a 6% agarose column, the canine-specific ELISA readily detected an antigen in the $V_0$ that coincided with a multimeric protein pattern typical of vWf:Ag.

Using pooled polyclonal mouse antidog vwf:Ag as an alternative sandwich antibody at a 1:100 dilution, dose-response curves were constructed for 11 of the survey plasmas at doubling dilutions from 1:25 to 1:1600. The relative cross-reactivity for vWf:Ag for this antibody system is shown in Table IV. Quantitation of vWf:Ag in vWd pig and human plasmas using this mouse sandwich antibody paralleled those shown in Table III for goat antidog vWf:Ag sandwich antibody.

Studies that employed 13 different Mabs prepared against porcine and bovine vWf:Ag as the capture reagent and goat antidog vWf:Ag as the sandwich antibody demonstrated that the plasmas of the 12 survey species reacted positively (greater than three times the average blank) in 54 of the 156 possible antibody combinations. The antibovine Mab #10/ goat antidog system reacted positively with plasmas of six species while the antiporcine Mab W1-5/goat antidog combination crossreacted positively with plasmas of 10 of the 12 species tested. The reactivities of these 12 plasmas with each Mab/goat antidog combination is reported in Table V.

The very strong reaction of rabbit plasma with the antiporcine Mabs W1-1, W1-2, W1-5 was further investigated by partially purifying rabbit von Wille-brand factor by filtering 10 ml of pooled rabbit plasma over an agarose column as above and testing the fractions and serial dilutions of the starting plasma with each Mab/goat antidog combination. The factor VIII coagulant activity of the fractions was measured and found in the $V_0$ fractions. Each of the above porcine Mabs reacted with the rabbit plasma and the $V_0$ fractions. Construction of a rabbit plasma standard curve permitted the quantitation of the $V_0$ reactive antigen. Using the W1-5/goat antidog antibody combination, recovery of the reactive antigen was 76.9%. Sodium dodecyl sulfate agarose-gel electrophoresis and immunoblotting of the rabbit plasma agarose filtration fractions utilizing the same sandwich and conjugate antibodies as in the above ELISA demonstrated the presence of high-, intermediate-, and low-molecular-weight multimers in rabbit plasma as well as their presence in the various fractions.

When the order of applying antiporcine and anti-bovine Mabs was reversed and they were used as sandwich antibodies, with rabbit antidog vWf:Ag serving as the capture reagent, the pattern of reactivities changed, as shown in Table VI. Antibovine Mab #10 and antiporcine Mab W1-5 still generated the highest percentage of cross reactivities; 10 of the 13 Mabs now reacted positively against their respective homologous antigens. However no reactivity with rabbit plasma was observed when the Mabs and rabbit anticanine vWf:Ag were in the sandwich and capture configuration, respectively.

Using rabbit antihuman vWf:Ag as the capture antibody and antibovine Mab #16 as the sandwich antibody, canine and porcine plasma vWf:Ag was quantitated in five samples from each species. The vWf:Ag levels of these plasma samples were also determined by porcine or canine specific ELISAs. The results of these assays are reported in Table III and demonstrate that the vWf:Ag levels measured in the mixed antibody systems were parallel to the ELISA using species-specific antibodies.

Thus, using antibodies specific for canine vWf:Ag, applicants found that numerous other mammalian plasmas were reactive in this assay configuration. The detected antigen from cat, rat, and guinea pig plasma eluted in the $V_0$ from agarose filtrations, suggesting that the reactive protein in these plasmas was von Willebrand factor. Specificity for the von Willebrand factor protein was confirmed by the fact that type III canine and porcine vWd and human von Willebrand factor-depleted plasmas are nonreactive. Porcine and human type I vWd plasmas demonstrated parallel reductions of vWf:Ag when assayed in the canine system or in their homologous antibody systems. Collectively these data indicated that the canine-specific ELISA detects the vWf:Ag of many other species. This ELISA antibody system was used in combination with other diagnostic assays to confirm, for the first time, type III vWd in the horse.

With the canine ELISA described above, applicants were able to also construct dose-response curves for 11 survey plasmas in which the lower limit of detection is at least $1.5 \times 10^{-3}$ un/ml for each species. These data demonstrate the potential of quantitating vWf:Ag in each of these species without the need for species-specific antibodies. This assay can be especially useful for small laboratory animals such as guinea pigs, rats, and mice for which it is difficult to prepare sufficient quantities of immunogen, or for rare or wild species in which plasma is not readily available for immunogen preparation. Using this technique, applicants have developed a quantitative ELISA for mouse vWf:Ag and have recently identified hypothyroid mice with reduced levels of plasma vWf:Ag.

Species cross-reactivities in the ELISA were further evaluated by utilizing 13 different Mabs prepared against either bovine or porcine vWf:Ag as probes or capture antibodies. The data presented in Tables V and VI demonstrate both the species-related differences in reactivity as well as reactive epitope conservation across species lines. Furthermore, these results clearly indicate that cross-reactivity is not exclusive to the canine polyclonal antibody system.

For those species reactive with a single but not other Mabs it is clear that the capture antibody was the non-reactive component in the antibody-antigen-antibody combination. The observation that cow and mouse plasma were unreactive in each of the 13 Mab capture systems may not reflect a lack of reaction with the capture antibodies, but rather a weak interaction with the sandwich antibody. Cow and mouse plasma also appeared unreactive in the canine polyclonal system, when the same concentration of goat antibody was used as sandwich antibody.

A parallel response pattern for dog and cat plasmas was observed with each of the six antibovine Mabs, which suggested similar immunologic regions for the vWf:Ag of these two species. This is reinforced by the observation that the vWf:Ag of cat plasma is one of the few heterologous vWf:Ags readily measured in the Laurell electro-immunoassay system using rabbit anticanine vWf:Ag (20).

In solid phase/capture antibody configuration, antiporcine Mabs W1-4, W1-8, and W1-16 were highly species-specific and exhibited little interspecies reactions. In contrast antiporcine Mabs W1-1, W1-2, and W1-5 each showed considerable and similar cross reactivity, exhibiting positive interactions with guinea pig, horse, monkey, sheep, pig, dog, goat and rabbit plasmas. The parallel reactivities for cat and dog vWf:Ag were again observed, however the W1-2 Mab captures canine, but not feline vWf:Ag.

Of interest was the finding that W1-1, W1-2, and W1-5 Mabs each reacted with a rabbit plasma antigen, then reacted with goat antidog vWf:Ag in liquid phase. The three antiporcine Mabs also reacted with partially purified rabbit von Willebrand factor.

The goat antidog reactivity with the rabbit V. protein suggested that this antibody could be used to identify rabbit vWf multimers. Sodium dodecyl sulfate-electrophoresis and electroblotting of rabbit plasma and agarose $V_0$ fractions demonstrated the typical vWf:Ag multimer patterns for the samples. These findings confirm that the above ELISA antibody system was detecting rabbit vWf:Ag. When used in combination with multimer electrophoresis these techniques provide sensitive qualitative and quantitative methods for the analysis of rabbit von Willebrand factor.

When the Mabs to bovine and porcine vWf:Ag were used in the reverse configuration as sandwich instead of capture antibodies, five of six anti-bovine Mabs now reacted positively with cow plasma and suggested that the lack of reaction in the capture configuration may have been caused either by a weakly reacting sandwich antibody or by the solid/liquid phase differences that exist for some Mabs against vWf:Ag (22). The most striking example of this difference is antiporcine Mab W1-4, which is nonreactive with pig plasma in the solid/capture phase, but has the highest affinity of the seven antiporcine Mabs with pig plasma when used in the liquid/sandwich phase.

Using five different antihuman Mabs against vWf, Hornsey reported that in a liquid phase assay the sera of ox, pig, dog, rabbit, sheep, chicken, donkey, goat, and rat were all unreactive, while human sera showed reactivity with all five antihuman Mabs (35). In a limited study, matched plasma and serum samples from a dog, human, and pig with normal plasma vWf:Ag levels were compared in three different ELISAs using antibodies specific for each species vWf. Applicants found that the three plasmas were strongly reactive in each ELISA antibody system, however the three serum samples were unreactive with either the homologous or heterologous antibody configurations.

Preliminary data suggested that polyclonal antibodies prepared in rabbits, goats, and mice to canine vWf:Ag will react with their homologous vWf:Ag (i.e. goat antidog vWf:Ag reacting with goat vWf:Ag) if the antibodies are used in liquid, but not solid phase. This was tested by using the rabbit, goat, or mouse anticanine vWf reagents as either capture or sandwich antibodies. In each case the homologous vWf:Ag reacted strongly with its respective antibody in the liquid, but not solid phase.

A mixed antibody system of rabbit antihuman vWf:Ag as capture antibody and antibovine Mab #16 as sandwich antibody was used to measure canine and porcine vWf:Ag. The parallel results for the canine- and porcine-specific assays demonstrated the potential for developing quantitative ELISAs using species-heterologous systems. The lower limit of vWf:Ag detection in the four mixed ELISA systems reported was at least $1.5 \times 10^{-3}$ un/ml.

TABLE II

ELISA Cross-reactivities of mammalian plasmas using antibodies specific for canine von Willebrand factor. Plasmas were diluted 1:100 (A) and 1:1000 (B).

| | ABSORBANCE AT 490 nm Sandwich Antibody Dilution | | | | | |
|---|---|---|---|---|---|---|
| | 1:10 | | 1:100 | | 1:1000 | |
| SPECIES | A | B | A | B | A | B |
| Guinea Pig | 1.775 | 0.976 | 1.189 | 0.419 | 0.480 | 0.207 |
| Dog | >4.000 | 1.212 | 2.829 | 0.683 | 1.610 | 0.486 |
| Cow | 1.123 | 0.967 | 0.308 | 0.305 | 0.155 | 0.145 |
| Horse | 1.944 | 0.961 | 1.000 | 0.435 | 0.279 | 0.133 |
| Cat | 2.916 | 1.310 | 2.455 | 0.803 | 1.136 | 0.345 |
| Monkey | 2.242 | 1.155 | 1.552 | 0.563 | 0.512 | 0.209 |
| Sheep | 1.571 | 0.748 | 0.898 | 0.350 | 0.903 | 0.230 |
| Pig | 2.089 | 1.072 | 1.277 | 0.470 | 0.362 | 0.180 |
| Rat | 1.046 | 0.738 | 0.765 | 0.379 | 0.290 | 0.157 |
| Goat | 1.577 | 0.670 | 1.219 | 0.396 | 1.265 | 0.280 |
| Mouse | 0.811 | 0.605 | 0.430 | 0.231 | 0.214 | 0.136 |
| Manatee | 1.061 | 0.414 | 0.799 | 0.300 | 0.300 | 0.159 |

TABLE III

Human, porcine, and canine plasma vWF:Ag levels (%) determined by ELISA in specific and mixed antibody systems.

| Capture Antibody Sandwich Antibody | Rabbit AD Goat AD | Rabbit AH Goat AH | Rabbit AP APM/W1-4 | Rabbit AH ASH/#16 |
|---|---|---|---|---|
| SAMPLE | | | | |
| human-BR | 95 | 89 | — | — |
| human-DW | 51 | 39 | — | — |
| human-SF | 64 | 57 | — | — |
| human-CA | 0.00 | 0.00 | — | — |
| pig-2330 | 30 | — | 30 | 34 |
| pig-2340 | 19 | — | 24 | 38 |

TABLE I

MASTER CHART

| | 1 | 2 | 3 | 4 | 5 | 6 | 7 | 8 | 9 | 10 | 11 | 12 |
|---|---|---|---|---|---|---|---|---|---|---|---|---|
| A | STD 1 | STD 2 | STD 3 | STD 5 | STD 5 | 83 Ref | 83 Ref | BLK | BLK | STD 3 | STD 2 | STD 1 |
| | 1.182 | 0.997 | 0.773 | 0.597 | 0.446 | 0.729 | 0.774 | 0.225 | 0.223 | 0.735 | 0.951 | 1.269 |
| | | | | | | 71% | 80% | | | | | |
| B | Sple 1 | Sple 1 | Sple 1 | Sple 2 | Sple 2 | Sple 2 | Sple 3 | Sple 3 | Sple 3 | Sple 4 | Sple 4 | Sple 4 |
| | 0.869 | 0.862 | 0.785 | 0.767 | 0.758 | 0.765 | 0.549 | 0.572 | 0.561 | 0.614 | 0.642 | 0.663 |
| | 103% | 101% | 83% | 79% | 77% | 79% | 37% | 41% | 39% | 49% | 54% | 58% |
| C | Sple 5 | Sple 5 | Sple 5 | Sple 6 | Sple 6 | Sple 6 | Sple 7 | Sple 7 | Sple 7 | Sple 8 | Sple 8 | Sple 8 |
| | 0.296 | 0.280 | 0.261 | 0.646 | 0.658 | 0.623 | 0.537 | 0.517 | 0.528 | 0.733 | 0.737 | 0.788 |
| | 0% | 0% | 0% | 55% | 57% | 50% | 35% | 31% | 33% | 72% | 73% | 84% |
| D | Sple 9 | Sple 9 | Sple 9 | Sple 10 | Sple 10 | Sple 10 | Sple 11 | Sple 11 | Sple 11 | Sple 12 | Sple 12 | Sple 12 |
| | 0.845 | 0.745 | 0.706 | 0.248 | 0.269 | 0.264 | 0.705 | 0.687 | 0.706 | 0.635 | 0.648 | 0.731 |
| | 97% | 74% | 66% | 0% | 0% | 0% | 66% | 63% | 66% | 53% | 55% | 71% |
| E | Sple 13 | Sple 13 | Sple 13 | Sple 14 | Sple 14 | Sple 14 | Sple 15 | Sple 15 | Sple 15 | Sple 16 | Sple 16 | Sple 16 |
| | 0.690 | 0.659 | 0.657 | 0.358 | 0.356 | 0.361 | 0.732 | 0.688 | 0.716 | 0.281 | 0.303 | 0.319 |
| | 63% | 57% | 57% | 6% | 5% | 6% | 72% | 63% | 68% | 0% | 0% | 0% |
| F | Sple 17 | Sple 17 | Sple 17 | Sple 18 | Sple 18 | Sple 18 | Sple 19 | Sple 19 | Sple 19 | Sple 20 | Sple 20 | Sple 20 |
| | 0.924 | 0.922 | 0.853 | 0.318 | 0.327 | 0.320 | 0.378 | 0.355 | 0.361 | 0.369 | 0.375 | 0.490 |
| | 117% | 116% | 99% | 0% | 1% | 0% | 9% | 5% | 6% | 7% | 8% | 27% |
| G | Sple 21 | Sple 21 | Sple 21 | Sple 22 | Sple 22 | Sple 22 | Sple 23 | Sple 23 | Sple 23 | Sple 24 | Sple 24 | Sple 24 |
| | 0.972 | 0.927 | 0.902 | 0.843 | 0.836 | 0.840 | 0.616 | 0.584 | 0.549 | 0.627 | 0.614 | 0.666 |
| | 118% | 118% | 111% | 96% | 95% | 96% | 49% | 43% | 37% | 51% | 49% | 58% |
| H | STD 4 | STD 5 | AC | AC | AC | 83 Ref | BLK | STD 5 | STD 4 | STD 3 | STD 2 | STD 1 |
| | 0.688 | 0.499 | 0.231 | 0.214 | 0.241 | 0.768 | 0.251 | 0.484 | 0.624 | 0.783 | 1.001 | 1.071 |
| | | | 0% | 0% | 0% | 79% | | | | | | |

TABLE III-continued

Human, porcine, and canine plasma vWF:Ag levels (%) determined by ELISA in specific and mixed antibody systems.

| Capture Antibody<br>Sandwich Antibody | Rabbit AD<br>Goat AD | Rabbit AH<br>Goat AH | Rabbit AP<br>APM/W1-4 | Rabbit AH<br>ASH/#16 |
|---|---|---|---|---|
| pig-2385 | 24 | — | 25 | 33 |
| pig-2389 | 15 | — | 24 | 31 |
| pig-2353 | 0.00 | — | 0.08 | 0.13 |
| dog-1130.7 | 51 | — | — | 49 |
| dog-1131 | 61 | — | — | 58 |
| dog-1133 | 27 | — | — | 31 |
| dog-1136.5 | 3.3 | — | — | 2.7 |
| dog-SC | 0.00 | — | — | 0.00 |

AD - antidog vWF, AH - antihuman vWF, AF - antipig vWF, APM - antipig Mab, ABM - antibovine Mab

TABLE IV

ELISA cross-reactivities of mammalian plasmas by ELISA using rabbit (capture) and mouse (sandwich) antibodies Specific for canine von Willebrand factor.

ABSORANCE AT 490 nm

| | PLASMA DILUTION | | | | | | | | OPD<br>REACTION |
|---|---|---|---|---|---|---|---|---|---|
| Species | 1:25 | 1:50 | 1:100 | 1:200 | 1:400 | 1:800 | 1:1600 | BLANK | TIME |
| Guinea Pig | 0.792 | 0.685 | 0.494 | 0.374 | 0.329 | 0.286 | 0.236 | 0.206 | 15 min |
| Cow | 1.027 | 0.739 | 0.526 | 0.360 | 0.269 | 0.264 | 0.211 | 0.203 | 13 |
| Horse | 1.022 | 0.780 | 0.596 | 0.481 | 0.227 | 0.251 | 0.226 | 0.193 | 12 |
| Cat | 0.879 | 0.640 | 0.560 | 0.400 | 0.262 | 0.260 | 0.161 | 0.114 | 6 |
| Monkey | 0.969 | 0.852 | 0.700 | 0.464 | 0.272 | 0.217 | 0.220 | 0.161 | 11 |
| Sheep | 0.889 | 0.790 | 0.678 | 0.550 | 0.293 | 0.206 | 0.197 | 0.134 | 8 |
| Pig | 0.887 | 0.737 | 0.604 | 0.470 | 0.364 | 0.305 | 0.230 | 0.144 | 8 |
| Rat | 0.718 | 0.587 | 0.462 | 0.383 | 0.340 | 0.277 | 0.525 | 0.231 | 20 |
| Dog | 1.099 | 0.924 | 0.788 | 0.630 | 0.450 | 0.340 | 0.210 | 0.120 | 5 |
| Mouse | 0.804 | 0.620 | 0.433 | 0.347 | 0.294 | 0.262 | 0.253 | 0.257 | 20 |
| Goat | 0.992 | 0.866 | 0.688 | 0.432 | 0.230 | 0.259 | 0.232 | 0.164 | 10 |
| Rabbit | 0.230 | 0.206 | 0.234 | 0.234 | 0.222 | 0.198 | 0.222 | 0.225 | 20 |

OPD - o-phenylenediamine dihydrochloride

TABLE V

Cross-reactivities of mammalian plasmas in an vWF:Ag ELISA using Mabs as the capture antibody and goat antidog vWF:Ag as the sandwich antibody.

| CAPTURE ANTIBODY: | G. Pig | Cow | Horse | Cat | Monkey | Sheep | Pig | Rat | Dog | Mouse | Goat | Rabbit |
|---|---|---|---|---|---|---|---|---|---|---|---|---|
| | | | | | Ratio of Absorbance to Blank | | | | | | | |
| Antibovine Mabs | | | | | | | | | | | | |
| 1-AF (3/16/83) | 2 | 2 | 3 | 10 | 2 | 4 | 2 | 2 | 8 | 2 | 3 | 5 |
| 2-AF (5/31/83) | 1 | 2 | 1 | 1 | 1 | 3 | 2 | 2 | 2 | 2 | 4 | 8 |
| 6-AF (4/16/87) | 1 | 2 | 5 | 9 | 2 | 4 | 2 | 1 | 10 | 1 | 3 | 4 |
| 7-AF (5/31/83) | 1 | 1 | 5 | 10 | 1 | 3 | 1 | 1 | 9 | 1 | 2 | 4 |
| 16-AF (1/14/83) | 2 | 1 | 1 | 3 | 1 | 2 | 2 | 1 | 4 | 1 | 2 | 1 |
| 10-AS (4/16/87) | 7 | 2 | 2 | 12 | 1 | 5 | 10 | 2 | 11 | 2 | 4 | 3 |
| Antiporcine Mabs | | | | | | | | | | | | |
| W1-3-AF | 3 | 1 | 1 | 17 | 13 | 2 | 10 | 1 | 16 | 1 | 2 | 3 |
| W1-4-AF | 1 | 1 | 1 | 1 | 1 | 1 | 1 | 1 | 1 | 1 | 1 | 6 |
| W1-8-AF | 1 | 1 | 1 | 1 | 1 | 2 | 5 | 1 | 1 | 1 | 1 | 1 |
| W1-1-IgG | 7 | 2 | 12 | 2 | 17 | 9 | 13 | 1 | 1 | 2 | 4 | 14 |
| W1-2-IgG | 7 | 2 | 7 | 2 | 11 | 11 | 9 | 3 | 13 | 2 | 4 | 12 |
| W1-5-IgG | 8 | 1 | 6 | 11 | 4 | 5 | 7 | 7 | 17 | 3 | 6 | 13 |

AF - Ascitic fluid, IgG - IgG fraction of AF, AS - $(NH_4)_2SO_4$ fraction of AF

TABLE VI

Cross-reactivities of mammalian plasmas in an vWF:Ag ELISA using rabbit antidog vWF:Ag as the capture antibody and Nabs against bovine or porcine VWF:Ag as the sandwich antibody.

| SANDWICH ANTIBODY: | G. Pig | Cow | Horse | Cat | Monkey | Sheep | Pig | Rat | Dog | Mouse | Goat | Rabbit |
|---|---|---|---|---|---|---|---|---|---|---|---|---|
| | | | | | Ratio of Absorbance to Blank | | | | | | | |
| Antibovine Mabs | | | | | | | | | | | | |
| 1-AF (3/16/83) | 2 | 4 | 2 | 3 | 2 | 4 | 2 | 2 | 2 | 2 | 3 | 2 |
| 2-AF (5/31/83) | 2 | 4 | 2 | 2 | 2 | 3 | 2 | 2 | 2 | 2 | 3 | 2 |
| 6-AF (4/16/87) | 2 | 4 | 2 | 3 | 2 | 4 | 2 | 2 | 2 | 2 | 3 | 2 |
| 7-AF (5/31/83) | 2 | 4 | 2 | 3 | 2 | 4 | 2 | 2 | 3 | 2 | 4 | 2 |
| 16-AF (1/14/83) | 3 | 3 | 2 | 5 | 2 | 4 | 4 | 2 | 7 | 2 | 4 | 2 |
| 10-AS (4/16/87) | 3 | 6 | 3 | 6 | 3 | 6 | 4 | 3 | 7 | 3 | 6 | 3 |
| Antiporcine Mabs | | | | | | | | | | | | |
| W1-3-AF | 3 | 2 | 2 | 4 | 3 | 3 | 3 | 2 | 3 | 2 | 3 | 2 |
| W1-4-AF | 3 | 3 | 3 | 7 | 7 | 3 | 8 | 3 | 2 | 3 | 3 | 3 |
| W1-8-AF | 3 | 3 | 3 | 3 | 3 | 3 | 4 | 3 | 3 | 3 | 3 | 3 |
| W1-1E-AF | 2 | 2 | 2 | 2 | 2 | 2 | 5 | 2 | 2 | 2 | 2 | 2 |
| W1-1-IgG | 3 | 2 | 3 | 2 | 2 | 2 | 3 | 2 | 2 | 2 | 2 | 2 |
| W1-2-IgG | 2 | 2 | 2 | 2 | 2 | 3 | 4 | 2 | 3 | 2 | 2 | 2 |
| W1-5-IgG | 3 | 3 | 4 | 4 | 2 | 4 | 4 | 2 | 6 | 2 | 4 | 2 |

AF - Ascitic fluid, IgG - IgG fraction of AF, AS - $(NH_4)_2SO_4$ fraction of AF

EXAMPLE 2
Coagulation factor VIII

An assay configuration has also been utilized for the detection of canine factor VIII by ELISA. The use of the described assay configuration allows for the immunologic quantitative and specific detection of canine factor VIII in plasma and tissue culture media. Furthermore, the detector reactant (i.e. monoclonal antibody to human factor VIII) can be utilized in the described assay configuration to manipulate specificity. Thus, it is possible to analyze the presence of trace amounts of human factor VIII in canine plasma, without the interference of the dogs own factor VIII in the assay. This is important in studies to develop gene therapies for coagulation factors where animals are used in combination with the human gene for factor VIII.

In one embodiment of the assay, the capture antibody that was used reacted with human Factor VIII but not canine Factor VIII. Therefore, measurement of the captured human Factor VIII could be made in the presence of canine Factor VIII. Similarly, another capture antibody was used to capture only canine Factor VIII.

Specifically, a capture antibody was used that would react with human (Esh 4), but would not capture the canine. Therefore, when measurements were taken only the captured human was detected.

In the case of the canine assay, a murine monoclonal antibody (Esh 7) was used as the capture antibody.

EXAMPLE 3
Reproductive hormones

Since structurally related hormones are important in human and veterinary reproductive biology and medicine, quantitation of specific metabolites is essential. These compounds share the necessary variable and conserved epitopes to make their analysis possible using the ELISA assay configuration disclosed herein. A similar system could be constructed to analyze class-specific anti-spermatozoa antibodies.

EXAMPLE 4
Acute phase proteins

Like vWf, other acute phase proteins have been identified and are important in many disease processes. They share conserved and variable epitopes and could be analyzed with high specificity and sensitivity using the ELISA configuration.

EXAMPLE 5
Tumor markers

A variety of marker proteins have been identified in association with oncologic disease processes. The configuration of the ELISA is ideally suited to identify and quantitate these markers.

EXAMPLE 6
Quantitation of rheumatoid factors

Rheumatoid factors can also be analyzed using the configuration of the ELISA.

EXAMPLE 7
Toxin quantitation

The presence of trace amounts of toxins (pesticides, biologicals) in soil and water samples could be quantitated using the configuration of the assay as generally described, resulting in greater sensitivity and specificity over other available assays.

In the case of toxins, it may be desirable to detect all members of a class of compounds that are contaminants in a system without having to detect specific portions of the particular members within the class. For example, a sample of a soil mixture can be analyzed for the presence of particular toxins by using a class reactive molecule that would look for that class of toxins in the soil. This method increases the sensitivity of the assay, because detection of each individual toxin may not be possible if the individual toxin is present in trace amounts. Detection as a class thus increases sensitivity. You can then use a panel of specific reactants to detect the individual toxins, if desired. Note that the common part for class detection or individual detection doesn't necessarily have to be a toxic part; it is just a common structural redundancy. It has to be chemically or biochemically consistent throughout, so that the reactant can be designed to capture it. This gives a concentrating effect in terms of measurement.

As another example of a toxin, we may be looking at the pesticide DDT in soil, and the DDT has a conserved structural part. There is also another pesticide in the soil that is present in a trace amount that is a class member with DDT, which we are interested in. This other pesticide indicates that the soil has been contaminated with something else other than DDT, so the DDT actually represents background noise. The assay configuration allows for the capture of the other pesticide without capturing the DDT to increase specificity.

EXAMPLE 8

Classes of Drugs

Identification of alkaloid based drugs as well as other classes of drugs, due to redundant and variable structural features, is also possible using the ELISA in the described configuration. An example is a class of alkaloids called pyrrolizidine alkaloids. They have a common structure called the necine or the base part. They have a variable part called the necisic acid. One part of it is a very similar chemistry, while the other one differs markedly. The necine is similar, but the necisic acid portion is very different in each alkaloid and the pharmacological and physiological properties of that alkaloid will vary based on the change in the necisic acid.

EXAMPLE 9

Cytokines

Cytokine classes are all structurally related. The quantitation is usually restricted to a single class (i.e. interleukin 6, interleukin 8, etc.). The ELISA would allow for detection of cytokines in a single assay format with high sensitivity and specificity for the individual cytokine.

EXAMPLE 10

Parasites

Another example would be a polyclonal capture antibody to a parasitic family with species-specific monoclonal antibodies to identify the actual parasite species (e.g. blood parasites such as Trypanosomes, Piroplasms, and Malarias which affect many species including humans but have species-specific subtypes).

As should be apparent from the above examples, the assay configuration of the subject invention can be used with any class or analyte to be analyzed. All that is required is a structurally similar region homologous to all of the members in the class. The capture antibody is based on the homologous portion so that it captures all members of the class. The sandwich antibody is based on the variable portion which is specific to each particular analyte (for identification of particular analytes) or is based on another homologus portion (for identification of all class members). The capture antibody increases sensitivity to high levels because it amplifies the signal by concentrating the analyte or class on the microtiter plate.

Thus, you have the option of screening captured compounds for the presence of specific members of the class by using the sandwich antibody or reactant (reacts with the variable portions). After screening, quantitative assays can be done using standard curves and known concentrations of the analyte. On you can just look for a class of compounds if the class is of interest (i.e., where the homologous part is toxic).

Although preferred embodiments have been depicted and described herein, it will be apparent to those skilled in the relevant art that various modifications, additions, substitutions and the like can be made without departing from the spirit of the invention and these are therefore considered to be within the scope of the invention as defined in the following claims.

What is claimed:

1. An immunoassay for detecting members of a class of molecules in a sample, each member of the class having a homologous portion common to members of the class, each member of the class being from a different species, said method comprising:

a. obtaining a panel of antibodies generated to recognize and bind a plurality of members of the class, and which were not generated to recognize and bind the member included in the sample;

b. selecting an antibody from (a) having a high binding affinity for the member at the class included in the sample c. attaching the antibody selected in (b) to an immunological reaction surface;

d. adding the sample to the immunological reaction surface under conditions so that the attached antibody recognizes and binds a member of the class so as to form a complex, the attached antibody reacting with and binding the homologous portion of the class; and e. detecting the complex so bound thereby detecting members of a class.

2. The method of claim 1 wherein said class of molecules comprises an antigen.

3. The method of claim 2 wherein said antigen comprises von Willebrand factor antigen.

4. The method of claim 3 wherein said antigen is canine von Willebrand factor antigen.

5. The method of claim 1 wherein said class of molecules comprises a blood factor.

6. The method of claim 5 wherein said blood factor comprises coagulation-Factor VIII.

7. The method of claim 6 wherein said blood factor comprises canine coagulation Factor VIII.

8. The method of claim 1 wherein said class of molecules is selected from the group consisting of proteins, toxins, surface receptors, hormones, and cytokines.

9. The method of claim 1 wherein said class of molecules comprises an antigen having a conserved epitope as a homologous portion, and wherein said antibody comprises an antibody to said homologous portion.

10. The method of claim 1 wherein said detection in step (e) comprises attaching a label to the complex and detecting said label.

11. The method of claim 10 wherein said label is selected from the group consisting of an enzyme, a radioactive marker, and a fluorescent dye.

12. The method of claim 1 wherein said sample comprises serum plasma, cells or fluids.

13. The method of claim 1 wherein said immunological reaction surface comprises a test tube, a well, a bead, a rod, or a strip.

14. A method as claimed in claim 1 wherein the antibody is selected to be a monoclonal antibody.

* * * * *